US012758126B1

(12) United States Patent
Napoles et al.

(10) Patent No.: US 12,758,126 B1
(45) Date of Patent: Oct. 13, 2026

(54) SYSTEMS FOR DETERMINING GLUCOSE VALUES BASED ON TRANSDERMAL CARBON DIOXIDE EMISSION

(71) Applicant: AMAZON TECHNOLOGIES, INC., Seattle, WA (US)

(72) Inventors: Adrian Napoles, Bellevue, WA (US); David Heckerman, Bellevue, WA (US); Andreas Caduff, Los Altos, CA (US); Layne Christopher Price, Seattle, WA (US); Gezheng Wen, Bellevue, WA (US); William White, Federal Way, WA (US); Liam Bradshaw, Seattle, WA (US); Sujay Karanth, Vancouver (CA); Jenson Lee Keller, Seattle, WA (US); Seyedmehdi Sadatgoltabarestani, Kirkland, WA (US); Derek Li, Seattle, WA (US); Saranya Chandrasekaran, Milpitas, CA (US); Kyle Thomas Miller, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 213 days.

(21) Appl. No.: 18/536,653

(22) Filed: Dec. 12, 2023

(51) Int. Cl.
*A61B 5/00* (2006.01)
*A61B 5/0205* (2006.01)
(Continued)

(52) U.S. Cl.
CPC ........ *A61B 5/14532* (2013.01); *A61B 5/0205* (2013.01); *A61B 5/11* (2013.01);
(Continued)

(58) Field of Classification Search
CPC ..... A61B 5/14532; A61B 5/0205; A61B 5/11; A61B 5/441; A61B 5/7271; A61B 5/01;
(Continued)

(56) References Cited

U.S. PATENT DOCUMENTS

2016/0249838 A1* 9/2016 Cheng .................... A61B 10/00 600/364
2020/0113516 A1* 4/2020 Marasco .............. A61B 5/0836

OTHER PUBLICATIONS

Bjorntorp, Per, "Studies on Adipose Tissue from Obese Patients with or without Diabetes Mellitus II. Basal and Insulin-stimulated Glucose Metabolism", The Acta Medica Scandinavia, Nov. 8, 1965, 6 pgs. Retrieved from the Internet: URL: https://onlinelibrary.wiley.com/doi/abs/10.1111/j.0954-6820.1966.tb05452.x.
(Continued)

*Primary Examiner* — Tse W Chen
*Assistant Examiner* — Joseph A Tombers
(74) *Attorney, Agent, or Firm* — Athorus, PLLC

(57) ABSTRACT

A wearable device is used to determine a glucose value for a portion of a user's body based on carbon dioxide emitted from the skin at the location of the wearable device. The device housing includes openings for carbon dioxide emitted by the user to enter and exit and may control accumulation of carbon dioxide within the housing using a valve, or allow carbon dioxide in the housing to reach an equilibrium value before determining a glucose value. Other sensors may be used to determine physiological or environmental factors, such as ambient carbon dioxide or increased respiration of the user, responsive to which a modifier may be applied to the determined glucose value.

19 Claims, 6 Drawing Sheets

(51) Int. Cl.
*A61B 5/11* (2006.01)
*A61B 5/145* (2006.01)
*A61B 5/01* (2006.01)
*A61B 5/024* (2006.01)
*A61B 5/08* (2006.01)
*A61B 5/1455* (2006.01)

(52) U.S. Cl.
CPC ............ *A61B 5/441* (2013.01); *A61B 5/7271* (2013.01); *A61B 5/01* (2013.01); *A61B 5/024* (2013.01); *A61B 5/0816* (2013.01); *A61B 5/14517* (2013.01); *A61B 5/14542* (2013.01); *A61B 5/14546* (2013.01); *A61B 5/1455* (2013.01); *A61B 5/6801* (2013.01); *A61B 2560/0252* (2013.01); *A61B 2560/0257* (2013.01); *A61B 2560/0462* (2013.01); *A61B 2562/0219* (2013.01); *A61B 2562/0247* (2013.01); *A61B 2562/0271* (2013.01)

(58) Field of Classification Search
CPC ... A61B 5/024; A61B 5/0816; A61B 5/14517; A61B 5/14542; A61B 5/14546; A61B 5/1455; A61B 5/6801; A61B 2560/0252; A61B 2560/0257; A61B 2560/0462; A61B 2562/0219; A61B 2562/0247; A61B 2562/0271
See application file for complete search history.

(56) References Cited

OTHER PUBLICATIONS

Bray, et al., "Effect of diet and triiodothyronine on the activity of sn-glycerol-3-phosphate dehydrogenase and on the metabolism of glucoseand pyruvate by adipose tissue of obese patients", Mar. 19, 1969, 11 pgs. Retrieved from the Internet: URL: https://www.jci.org/articles/view/106107/pdf.

Bray, George A., "Lipogenesis in Human Adipose Tissue: Some Effects of Nibbling and Gorging", Aug. 9, 1971, 12 pgs. Retrieved from the Internet: URL: https://www.ncbi.nlm.nih.gov/pmc/articles/PMC302159/pdf/jcinvest00175-0085.pdf.

Cushman, et al., "Structure function relationships in the adipose cell. III. Effects of bovine serum albumin on the metabolism of glucose and the release of nonesterified fatty acids and glycerol", The Rockefeller University, Aug. 1970, 8 pgs. Retrieved from the Internet: URL: https://www.ncbi.nlm.nih.gov/pmc/articles/PMC2108009/pdf/354.pdf.

Davidson, Mayer B., "Effect of Obesity on Insulin Sensitivity of Human Adipose Tissue", UCLA School of Medicine and the Wadsworth General Hospital, 1972, 7 pgs.

Dole, Vincent P., et al., "A relation between non-esterified fatty acids in plasma and the metabolism of glucose", The Rockefeller Institute for Medical Research, Jul. 21, 1955, 6 pgs. Retrieved from the Internet: URL: https://www.jci.org/articles/view/103259/pdf.

Freychet, et al., "Impairment of insulin binding to the fat cell ,plasma membrane in the obese hyperglycemic", Jun. 5, 1972, 4 pgs. Retrieved from the Internet: URL: https://febs.onlinelibrary.wiley.com/doi/pdfdirect/10.1016/0014-5793%2872%2980519-2.

Gliemann, Jorgen, "Insulin-like Activity of Dilute Human Serum Assayed by an Isolated Adipose Cell Method", The Rockefeller Institute, Oct. 1965, 7 pgs. Retrieved from the Internet: URL: https://watermark.silverchair.com/14-10-643.pdf?token=AQECAHi208BE49Ooan9kkhW_Ercy7Dm3ZL_9Cf3qfKAc485ysgAAA0QwggNABgkqhkiG9w0BBwagggMxMIIDLQIBADCCAyYGCSqGSIb3DQEHATAeBglghkgBZQMEAS4wEQQMXtc8H2c1Q4l_KxFfAgEQgIlC96nvAVUbBakGqZ.

Goldrick, et al., "Lipolysis and lipogenesis from glucose in human fat cells of different sizes: Effects of insulin, epinephrine, and theophylline", the Department of Clinical Science, The John Curtin School of Medical Research, The Australian National University, Feb. 3, 1970, 12 pgs. Retrieved from the Internet: URL: https://www.jci.org/articles/view/106335/pdf.

Goldrick, et al., "Serial Studies on the Metabolism of Human Adipose Tissue. II. Effects of Caloric Restriction and Refeeding on Lipogenesis, and the Uptake and Release of Free Fatty Acids in Obese and Nonobese Individuals", The Rockefeller Institute, Jan. 27, 1964, 12 pgs. Retrieved from the Internet: URL: https://www.ncbi.nlm.nih.gov/pmc/articles/PMC441980/pdf/jcinvest00461-0075.pdf.

Grey, et al., "The Effect of Fasting, Diet, and Actinomycin D on Insulin Secretion in the Rat", Jul. 11, 1969, 9 pgs. Retrieved from the Internet: URL: https://www.ncbi.nlm.nih.gov/pmc/articles/PMC535760/pdf/jcinvest00221-0045.pdf.

Hirsch, et al., "Methods for the determination of adipose cell size in man and animals", The Rockefeller University, 1968, 10 pgs. Retrieved from the Internet: URL: https://www.jlr.org/article/S0022-2275(20)43151-7/pdf.

Hirsch, et al., "Serial Studies on the Metabolism of Human Adipose Tissue. I. Lipogenesis and Free Fatty Acid Uptake and Release in Small Aspirated Samples of Subcutaneous Fat", Rockefeller Institute, Jan. 27, 1964, 17 pgs. Retrieved from the Internet: URL: https://www.ncbi.nlm.nih.gov/pmc/articles/PMC441979/pdf/jcinvest00461-0058.pdf.

Hirsch, et al., "Studies of adipose tissue in man. A microtechnic for sampling and analysis", The Rockefeller Institute, Oct. 16, 1959, 14 pgs. Retrieved from the Internet: URL: https://www.researchgate.net/publication/9851658_Studies_of_adipose_tissue_in_man_A_microtechnic_for_sampling_and_analysis.

Hogstedt, et al., "Sampling insulin in different tissue compartments using microdialysis: methodological aspects", Dec. 15, 2020, 10 pgs. Retrieved from the Internet: URL: https://www.nature.com/articles/s41598-020-78728-x.

Jansson, et al., "Measurement by Microdialysis of the Insulin Concentration in Subcutaneous Interstitial Fluid", May 20, 1993, 5 pgs. Retrieved from the Internet: URL: https://diabetesjournals.org/diabetes/article/42/10/1469/8186/Measurement-by-Microdialysis-of-the-Insulin.

Knittle, et al., "Effect of Weight Reduction on in Vitro Adipose Tissue Lipolysis and Cellularity in Obese Adolescents and Adults", Mount Sinai School of Medicine, Department of Pediatrics, Devision of Nutrition and Metabolism, Jun. 1972, 8 pgs. Retrieved from the Internet: URL: https://watermark.silverchair.com/21-6-754.pdf?token=AQECAHi208BE49Ooan9kkhW_Ercy7Dm3ZL_9Cf3qfKAc485ysgAAAz8wggM7BgkqhkiG9w0BBwagggMsMIIDKAIBADCCAyEGCSqGSIb3DQEHATAeBglghkgBZQMEAS4wEQQMrull9N_KXah7ukGzAgEQgIlC8jujAwO9CMTxXrw.

Rabinowitz, et al., "Forearm metabolism in obesity and its response to intra-arterial insulin. Characterization of insulin resistance and evidence for adaptive hyperinsulinism.", The Johns Hopkins University and Hospital, Aug. 15, 1962, 9 pgs. Retrieved from the Internet: URL: https://dm5migu4zj3pb.cloudfront.net/manuscripts/104000/104676/JCI62104676.pdf.

Rapport, et al., "Photometric determination of fatty acid ester groups in phospholipids", Apr. 11, 1955, 6 pgs. Retrieved from the Internet: URL: https://www.jbc.org/article/S0021-9258(19)57169-1/pdf.

Rodbell, Martin, "Metabolism of isolated fat cells. I. Effects of hormones on glucose metabolism and lipolysis.", National Institutes of Health, National Institute of ARthritis and Metabolic Diseases, Laboratory of Nutrition and Endocrinology, Aug. 5, 1963, 6 pgs. Retrieved from the Internet: URL: https://www.jbc.org/article/S0021-9258(18)51687-2/pdf.

Salans, et al., "Glucose Metabolism and the Response to Insulin by Human Adipose Tissue in Spontaneous and Experimental Obesity: Effects of Dietary Composition and Adipose Cell Size", JCI The Journal of Clinical Investigation, 1974, pp. 848-856, 10 pgs. Retrieved from the Internet: URL: chrome-extension://efaidnbmnnnibpcajpcglclefindmkaj/https://dm5migu4zj3pb.cloudfront.net/manuscripts/107000/107625/cache/107625.1-20141229145632-covered-e0fd13ba177f913fd3156f593ead4cfd.pdf.

(56) References Cited

OTHER PUBLICATIONS

Salans, et al., "Experimental Obesity in Man: Cellular Character of the Adipose Tissue", Oct. 19, 1970, 7 pgs. Retrieved from the Internet: URL: https://www.ncbi.nlm.nih.gov/pmc/articles/PMC292021/pdf/jcinvest00194-0053.pdf.

Salans, et al., "Studies of Human Adipose Tissue: Adipose Cell Size and Number in Nonobese and Obese Patients", Dartmouth-Hitchcock Medical Center, Department of Medicine and Surgery, Sep. 21, 1972, 13 pgs. Retrieved from the Internet: URL: https://dm5migu4zj3pb.cloudfront.net/manuscripts/107000/107258/JCI73107258.pdf.

Salans, et al., "The effect of insulin upon glucose metabolism by adipose cells of different size: Influence of cell lipid and protein content, age, and nutritional state", Dartmouth-Hitchcock Medical Center, Department of Medicine, Oct. 6, 1970, 13 pgs. Retrieved from the Internet: URL: https://www.jci.org/articles/view/106623/pdf.

Salans, et al., "The Role of Adipose Cell Size and Adipose Tissue Insulin Sensitivity in the Carbohydrate Intolerance of Human Obesity", The Rockefeller University, Aug. 25, 1967, 13 pgs. Retrieved from the Internet: URL: https://www.ncbi.nlm.nih.gov/pmc/articles/PMC297156/pdf/jcinvest00236-0155.pdf.

Sims, et al., "Endocrine and Metabolic Adaptation to Obesity and Starvation", The Laurentian Hormone Conference, 1972, 3 pgs. Retrieved from the Internet: URL: https://www.sciencedirect.com/science/article/abs/pii/B9780125711296500166.

Smith, Ulf, "Effect of cell size on lipid synthesis by human adipose tissue in vitro", University of Gothenburg, Department of Clinical Chemistry, 1971, 6 pgs. Retrieved from the Internet: URL: https://www.jlr.org/action/showPdf?pii=S0022-2275%2820%2939547-X.

* cited by examiner

SYSTEMS FOR DETERMINING GLUCOSE VALUES BASED ON TRANSDERMAL CARBON DIOXIDE EMISSION

BACKGROUND

Changes in glucose for an individual may be caused by consumption of food or drink, medical conditions, physical activity, or other events. Detecting changes in glucose typically includes determining a blood glucose value for an individual by testing the individual's blood, which may be invasive, uncomfortable, and consume time and resources. Certain types of sensors may non-invasively determine values indicative of glucose in a user's body. However, physical and physiological characteristics of the user's body may interfere with determining an accurate glucose value based on signals from the sensors.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
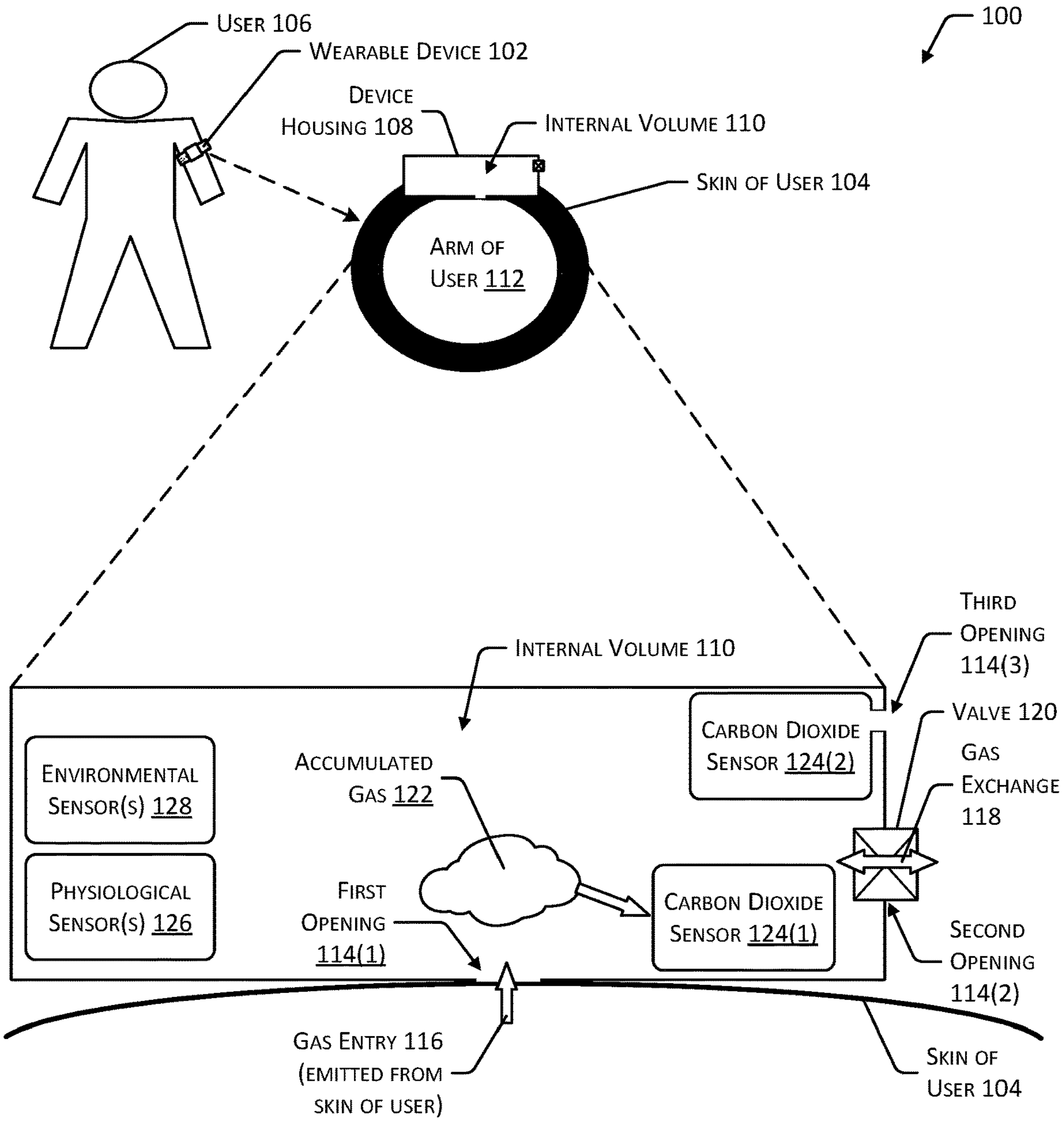
FIG. 1 is a diagram depicting an implementation of a wearable device that may be used to determine rates or quantities of transdermal carbon dioxide emitted from the skin of a user, which may be used to determine a value indicative of glucose associated with at least a portion of the body of the user.

While implementations are described in this disclosure by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used in this disclosure are for organizational purposes only and are not meant to be used to limit the scope of the description or the claims. As used throughout this application, the word "may" is used in a permissive sense (i.e., meaning having the potential to) rather than the mandatory sense (i.e., meaning must). Similarly, the words "include", "including", and "includes" mean "including, but not limited to".

DETAILED DESCRIPTION

Conventionally, changes in glucose associated with an individual may be determined based on a blood glucose value, which may be measured by extracting blood from the individual for analysis. This process is invasive, may cause physical discomfort, and may require use of specialized equipment or resources. Additionally, measurement of blood glucose may be affected by a variety of physiological factors, such as body temperature of the user, sweat or other sources of moisture at or near the location of a sensor, exercise or other physical movement of the user, slippage or other movement of a sensor relative to the user's body, and so forth. For example, if a user attempts to determine a change in glucose caused by a specific source, such as metabolism of food and drink, a blood glucose value may indicate an aggregate glucose value caused by multiple factors, which may obscure the effect of metabolism. Non-invasive methods for determining values indicative of glucose may include use of sensors that transmit signals into a portion of a user's body and determine characteristics of the signals. For example, radio frequency (RF) electrodes placed on the body may transmit signals into the body, while sensors or receivers may detect at least a portion of the transmitted signals and generate data indicative of signal characteristics. However, use of RF signals to determine values that may be used to infer the presence of glucose or other molecules may be subject to inaccuracy due to various physical and physiological characteristics of the user's body creating noise that may obscure the effect of glucose on the signal. Another method for non-invasively determining the presence of glucose may include detecting amounts of carbon dioxide or other molecules in the breath of an individual, based on the metabolism of glucose creating carbon dioxide and other products that may be exhaled. However, this method may be subject to inaccuracy due to various physiological characteristics of the user, and may detect an aggregate blood glucose value rather than a change in glucose caused specifically by metabolism.

Described in this disclosure are techniques for determining a glucose value, or other type of metabolic value, associated with a user by using a wearable sensor to detect a quantity or rate of transdermal carbon dioxide that passes through the skin of the user. When metabolism occurs within a cell, carbon dioxide is one product of the metabolic process. Most carbon dioxide produced in this manner enters the bloodstream for transport to the lungs. However, a portion of the carbon dioxide produced as a result of metabolism remains in the interstitial fluid between cells and exits the body by passing through the skin into the ambient environment outside of the body. The amount of carbon dioxide that passes through the skin and the rate at which carbon dioxide passes through the skin may be proportional to an amount of metabolism of glucose or other molecules that has occurred in the body. Therefore, measuring the amount or rate associated with transdermal carbon dioxide may be used to infer a metabolic value indicative of metabolized glucose in the body, or other substances that are able to be metabolized, such as fat or protein. For example, the amount or rate associated with transdermal carbon dioxide may be used to determine a total amount of metabolism of glucose in combination with metabolism of other substances. Continuing the example, increased dietary carbohydrate intake is associated with an increased basal rate of glucose metabolism and response to insulin by adipose cells. One or more modifiers may be applied to this total value to determine a value indicative of metabolized glucose.

A wearable device may contain a carbon dioxide sensor within a housing. The housing may have one or more first openings that face the body of the user when worn. For example, carbon dioxide emitted from the skin of the user may enter the housing of the wearable device through the first opening(s). The housing may have one or more second openings on a different portion that permit passage of carbon dioxide between an internal volume of the housing and the ambient environment external to the housing. The carbon dioxide sensor may determine sensor data indicative of a quantity of carbon dioxide within the housing, or a rate at which carbon dioxide accumulates in the housing.

In some implementations, the wearable device, or another computing device in communication with the wearable device, may determine that the quantity or rate has reached an equilibrium value (e.g., having a rate of change less than a threshold value), which may occur when the rate of accumulation of transdermal carbon dioxide through the first opening(s) and the rate of passage of carbon dioxide into the ambient environment through the second opening(s) are similar. In response to this determination, a value indicative of the quantity or rate associated with the carbon dioxide may be determined, then used to determine a glucose value. In other implementations, the wearable device, or another computing device in communication with the wearable device, may determine that the quantity or rate associated with carbon dioxide within the housing has deviated from an equilibrium value by at least a threshold amount. In response to this determination, a value indicative of the quantity or rate associated with the carbon dioxide may be determined, then used to determine a glucose value or other metabolic value.

In other implementations, a valve in a second opening in the housing may be used to control passage of carbon dioxide between the interior of the housing and the ambient environment. For example, the valve may be caused to move to an open position to enable passage of carbon dioxide, such as to purge the interior of the housing of accumulated carbon dioxide and enable the amount of carbon dioxide in the interior to establish equilibrium with the ambient environment. The valve may then be caused to move to a closed position to prevent passage of carbon dioxide through the second opening and enable carbon dioxide emitted from the skin of the user to accumulate within the housing. After a threshold length of time has elapsed, a value indicative of the quantity or rate associated with the accumulation of carbon dioxide in the housing may be determined, then used to determine a glucose value. In some cases, this process may be repeated multiple times, and the glucose value may be determined based on multiple carbon dioxide values to improve accuracy and reduce the effect of noise. In some implementations, an active or passive mechanism may be used to purge or otherwise displace carbon dioxide from the interior of the housing. For example, a pump, fan, piezoelectric device, or other gas-moving device may be used to move carbon dioxide from within the housing through the second opening into the ambient environment. As another example, a purge gas from a source volume that may be connected to the internal volume of the housing may be flowed into the housing to displace carbon dioxide. As yet another example, a semi-permeable membrane or other type of barrier that enables passage of carbon dioxide from the housing into the ambient environment but limits passage of gas into the housing may be positioned at the second opening.

In some implementations, multiple carbon dioxide sensors may be positioned at different locations on the body of the user to acquire data indicative of quantities or rates of emission of transdermal carbon dioxide. For example, the quantities of vascular structure, muscle tissue, skin, adipose tissue, and so forth may vary at different locations on the body, which may affect the rate or quantity of transdermal carbon dioxide that is emitted. Additionally, the distance of a particular location on the body from the heart, lungs, or other portions thereof may affect the amount of carbon dioxide associated with metabolism that may be detected. Determining a glucose value or other metabolic value based on multiple carbon dioxide values associated with different locations on the body may improve accuracy and reduce the effect of variance in tissue across the body on the glucose value.

A glucose value may be determined based on one or more relationships between emission of carbon dioxide from skin and metabolism of glucose. For example, the breakdown of one molecule of glucose typically yields six molecules of carbon dioxide. Based on the quantity of accumulated carbon dioxide within the volume of the housing over a selected period of time, or the rate at which the carbon dioxide accumulated, a glucose value indicative of a quantity of metabolized glucose may be inferred. In some implementations, a value indicative of metabolism of glucose and other substances that are able to be metabolized may be determined, and a value indicative of metabolized glucose may be determined by applying a modifier to this initial value. Because carbon dioxide that passes through the skin of a user (e.g., from the interstitial fluid of the body) is primarily a product of cellular metabolism at or near the location of the carbon dioxide sensor, the glucose value determined based on the quantity or rate associated with accumulation of carbon dioxide in the housing may primarily be associated with metabolism, which in some cases may differ from a general blood glucose measurement. For example, due to the presence of an endothelial barrier for insulin in subcutaneous tissue, lower insulin levels and a slower rise in interstitial fluid when compared to blood plasma may be observed. In some implementations, carbon dioxide that passes through the skin of the user may also be indicative of factors of glucose metabolism occurring in adipose cells. For example, the state of nutrition and adipose cell sizes of a user may influence basal and insulin-stimulated glucose metabolism in adipose tissue, which may in turn affect quantities of carbon dioxide emitted from the skin of the user.

In some cases, one or more physiological or environmental factors may affect the quantity or rate of emission of carbon dioxide from the skin of the user. One or more additional sensors may be used to determine physiological or environmental values, which may be used to determine a modifier that may be used, in combination with the determined quantity or rate of emission of carbon dioxide, to determine a glucose value that accounts for the physiological or environmental factors. For example, a second carbon dioxide sensor may be used to determine data indicative of ambient carbon dioxide external to the housing, which may be used to determine a modifier that may be used to modify the determined quantity or rate of carbon dioxide accumulation determined using the first carbon dioxide sensor, or the determined glucose value. As another example, physiological sensors, such as a temperature senor, blood oxygen sensor, heart rate sensor, respiratory rate sensor, photoplethysmography (PPG), accelerometer, moisture sensor, pressure sensor, sweat sensor, or ketone sensor may be used to determine physiological values associated with the user. For example, data indicative of blood oxygen, heart rate, and motion may indicate a high level of physical exertion or respiration of the user, which may affect emission of transdermal carbon dioxide. In such a case, a modifier may be determined which may affect the determined glucose value. As another example, the rate or quantity of carbon dioxide emitted from the skin of the user may be indicative of a total amount of metabolism of various molecules. A physiological sensor may be used to determine data indicative of ketones emitted from the skin of the user. A quantity or rate associated with emission of ketones may be used to determine a value associated with metabolism of fat, which may be used to determine a modifier to apply to the total amount of metabolism to determine a value indicative of glucose metabolism. As yet another example, the pressure applied to the body of a user by a wearable device may affect the rate or quantity of carbon dioxide emitted from the skin of the user, and a modifier associated with a pressure value determined using a pressure sensor may be applied to a determined glucose or other metabolic value.

Implementations described herein may determine glucose values or other metabolic values indicative of cellular metabolism by cells at or near the location of a wearable device based on transdermal carbon dioxide that is emitted from the skin of the user at or near the location of the wearable device. The determined glucose or other metabolic value(s) may be primarily indicative of metabolism and less affected by other factors that may occur in a blood glucose value, and less affected by physiological and environmental factors. However, other sensors may be used to determine physiological and environmental values, which may be used to modify the determined value(s) to further improve accuracy. A wearable device that contains the carbon dioxide sensor may include multiple openings in the housing, at least a first of which enables passage of carbon dioxide from the skin of the user into the housing. Other openings that communicate gas between the internal volume of the housing and the ambient environment may be controlled using one or more valves, or the device may be configured to determine glucose or other metabolic values based on measurements of equilibrium values or deviations from equilibrium values determined using the wearable device.

FIG. 1 is a diagram 100 depicting an implementation of a wearable device 102 that may be used to determine rates or quantities of transdermal carbon dioxide emitted from the skin of a user 104, which may be used to determine a value indicative of glucose associated with at least a portion of the body of the user 106. The wearable device 102 may include a device housing 108 that encloses one or more sensors within an internal volume 110. The device housing 108 may be secured to the body of the user 106 by a band or other type of securing mechanism, such as an adhesive, strap, patch, or article of clothing. In some implementations, the band or other mechanism for engaging the wearable device 102 to the body of the user 106 may include one or more fasteners, adjustable mechanisms, and so forth which may be used to control the tightness and amount of skin compression caused by contact between the wearable device 102 and the body of the user 106. FIG. 1 depicts the wearable device 102 secured about the arm of the user 106. However, in other implementations, the wearable device 102 may be secured to any portion of the body of the user 106. For example, the wearable device 102 may be secured to any peripheral appendage such as the upper arm, forearm, wrist, hand, upper leg, lower leg, ankle, foot, and so forth. In some implementations, multiple wearable devices 102 may be secured to different portions of the body of the user 106 and information acquired using the sensors of each wearable device 102 may be used to determine glucose values associated with the user 106.

The device housing 108 may include one or more first openings 114(1) in a first side thereof that faces the skin of the user 104 when the wearable device 102 is worn. Carbon dioxide that is emitted from the body of the user 106, through the skin, may pass through the first opening 114(1) and into the internal volume 110 of the device housing 108, represented by the arrow labeled as gas entry 116. While FIG. 1 depicts the device housing 108 including a single first opening 114(1), in other implementations, the device housing 108 may include multiple openings 114 through which carbon dioxide from the body of the user 106 may pass into the internal volume 110 of the device housing 108. The device housing 108 may include a second opening 114(2) that may enable the passage of carbon dioxide between the internal volume 110 of the device housing 108 and an ambient environment external to the device housing 108, represented by the arrow labeled as gas exchange 118. While FIG. 1 depicts the device housing 108 including a single second opening 114(2), in other implementations, the device housing 108 may include multiple openings 114 that enable the exchange of carbon dioxide between the internal volume 110 of the device housing 108 and the ambient environment external to the device housing 108.

In some implementations a valve 120 may be used to control the flow of gas through the second opening 114(2). For example, when the valve 120 is an open position, carbon dioxide may be exchanged between the interior and exterior of the device housing 108, which may enable equilibrium to be established between the interior and exterior. When the valve 120 is in a closed position, passage of gas through the second opening 114(2) may be prevented and carbon dioxide from the body of the user 106 that passes into the interior of the device housing 108 through the first opening 114(1) may accumulate within the device housing 108. Accumulated gas 122 within the internal volume 110 of the device housing 108 may be periodically or continuously measured using one or more carbon dioxide sensors 124. After determining a quantity of carbon dioxide within the internal volume 110 of the device housing 108, or a rate of accumulation of carbon dioxide within the internal volume 110, the valve 120 may be opened to enable carbon dioxide to exit the device housing 108 through the second opening 114(2).

In other implementations, use of a valve 120 may be omitted and gas may flow between the interior and exterior of the device housing 108 via the second opening 114(2). In such a case, carbon dioxide within the device housing 108 may reach equilibrium with the ambient environment external to the device housing 108. For example, when a rate of change of a quantity or rate of accumulation or carbon dioxide within the device housing 108 is less than a threshold value, this may indicate an equilibrium with the ambient environment. Sensor data determined using a carbon dioxide sensor 124(1) may be acquired when the rate of change associated with carbon dioxide is less than the threshold value. In other implementations, sensor data determined using the carbon dioxide sensor 124(1) may be acquired when the quantity or rate of change of carbon dioxide in the internal volume 110 deviates from the equilibrium state by at least a threshold amount. In some implementations, a first carbon dioxide sensor 124(1) may determine sensor data indicative of carbon dioxide within the internal volume 110 of the device housing 108, a second carbon dioxide sensor 124(2) may determine sensor data indicative of ambient carbon dioxide via a third opening 114(3) in the device housing 108, and a modifier may be determined based on the sensor data from the second sensor. The modifier may be used to modify the sensor data determined using the first carbon dioxide sensor 124(1) or to determine a glucose value based on the data from the first carbon dioxide sensor 124(1). For example, a value based on data from the second carbon dioxide sensor 124(2) may be subtracted from a value based on data from the first carbon dioxide sensor 124(1). In other implementations, a single carbon dioxide sensor 124 may determine sensor data indicative of carbon dioxide within the device housing 108 and carbon dioxide external to the device housing 108. In still other implementations, more than two carbon dioxide sensors 124 may be used.

In some implementations, the wearable device 102 may include one or more physiological sensors 126 that may determine physiological data indicative of one or more physiological values associated with the user 106. For example, a physiological sensor 126 may include one or more of a heart rate sensor, a blood oxygen sensor, an accelerometer, a motion sensor, a location sensor, a moisture sensor, a sweat sensor, a blood pressure sensor, a PPG, a respiration sensor, or a ketone sensor. Physiological values determined using the physiological sensor(s) 126 may be used to determine a modifier that may affect a glucose value determined based on data from the carbon dioxide sensor 124(1). For example, physiological values indicative of physical exertion or increased respiratory rate may be used to determine a negative modifier associated with the quantity or rate of carbon dioxide determined using the carbon dioxide sensor 124(1). As another example, physiological values indicative of movement greater than a threshold amount may be used to determine a modifier to data from the carbon dioxide sensor 124(1) or to the determined glucose value. As yet another example, physiological values indicative of increased body temperature or the presence of sweat or other moisture at the location of the wearable device 102 may be used to determine a modifier to data from the carbon dioxide sensor 124(1) or to the determined glucose value. Continuing the example, the presence of sweat on the body of the user at or near the location of the sensor may affect a signal indicative of electrical impedance. This signal may be represented as a graph that indicates signal value (e.g., KHz) versus time. The first derivative of this graph may be used to determine peaks having a width that represents periods of time when sweat was present, and a corresponding change in the electrical signal at the determined times may be used to determine a modifier to be applied to values determined using the carbon dioxide sensor 124(1). In one implementation, a physiological value indicative of a quantity or rate of emission of ketones from the body of the user 106 may be used to determine a modifier to data from the carbon dioxide sensor 124(1) to account for metabolism of fat, enabling a more accurate glucose value to be determined. For example, a wearable electrochemical sensor may use electrical signals to detect amounts of beta hydroxybutyrate (BHB) or other ketone bodies or related molecules in the body, such as in sweat or interstitial fluid.

In some implementations, the wearable device 102 may include one or more environmental sensors 128 that may determine environmental data indicative of one or more environmental values associated with the ambient environment proximate to the wearable device 102. For example, environmental sensors 128 may include temperature sensors, pressure sensors, light sensors, gas sensors, sensors configured to detect the presence or quantities of particular molecules, and so forth. For example, a barometric sensor may be used to determine pressure of the ambient atmosphere. Based on data from the environmental sensor(s) 128, one or more modifiers to data from the carbon dioxide sensor 124(1) or to the determined glucose value may be applied. For example, air pressure external to the device housing 108 may affect the quantity of carbon dioxide that accumulates within the device housing 108 or the rate of accumulation, and a positive modifier may be applied to the data from the carbon dioxide sensor 124(1) to account for the determined environmental value.

Figure 2:
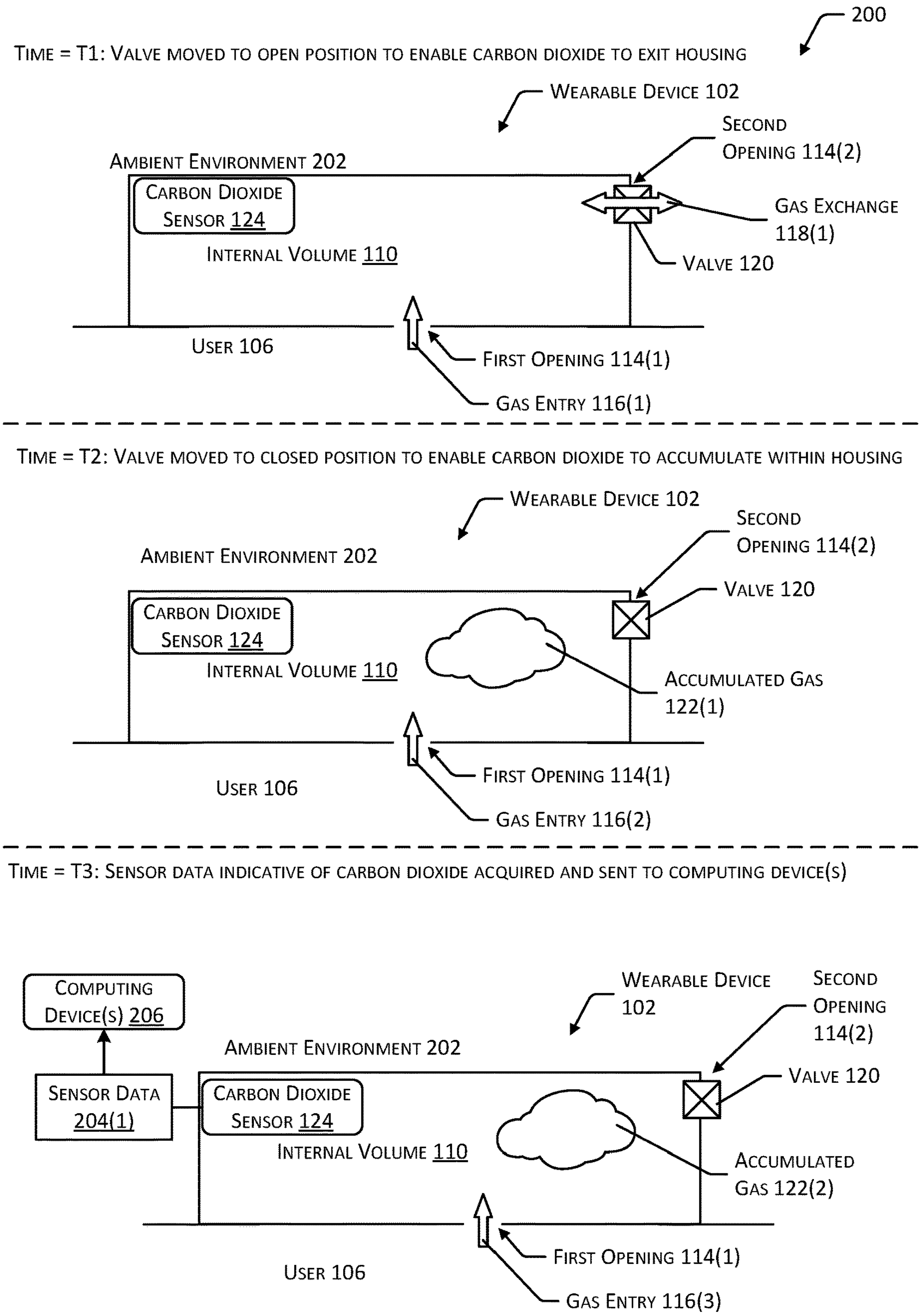
FIG. 2 is a diagram depicting an implementation of a method for determining rates or quantities of transdermal carbon dioxide emitted from the skin of a user that includes controlling the passage of gas using a valve.

FIG. 2 is a diagram 200 depicting an implementation of a method for determining rates or quantities of transdermal carbon dioxide emitted from the skin of a user 104 that includes controlling the passage of gas using a valve 120. As described with regard to FIG. 1, in some implementations, a wearable device 102 may include a device housing 108 having a first opening 114(1) that faces a body of the user 106 when worn, and a second opening 114(2) that may enable exchange of gas between the internal volume 110 of the device housing 108 and an ambient environment 202 external to the device housing 108. A valve 120 may be used to control the passage of gas through the second opening 114(2). For example, the valve 120 may enable a gas exchange 118(1) between the internal volume 110 and the ambient environment 202 when in an open position and prevent a gas exchange 118 when in a closed position. As such, the valve 120 may be used to purge at least a portion of the accumulated gas 122 within the internal volume 110 into the ambient environment 202 when the concentration of gas within the internal volume 110 exceeds that of the ambient environment 202, until an equilibrium state is reached between the internal volume 110 and the ambient environment 202. In some implementations, one or more purging mechanisms may be used to evacuate gas from the internal volume 110 toward the ambient environment 202. For example, a purging mechanism may include a pump, a fan, a vibrating element such as a ceramic disc, and so forth. As another example, a purging mechanism may include a reservoir that contains a purging gas that may be secured to the internal volume 110 to flow the purging gas therein and displace carbon dioxide. In some cases, a passive purging mechanism such as a membrane that is permeable to carbon dioxide may be placed within the second opening 114(2). In some implementations, one or more purging mechanisms may be user-actuated. For example, movement of the user 106 may flex or compress a flexible portion of the device housing 108, causing the internal volume 110 to vent gas through one or more valves 120.

At a first time T1, the valve 120 may be moved to an open position to enable carbon dioxide to exit the device housing 108. For example, with the valve 120 in the open position, a gas exchange 118(1) between the internal volume 110 and ambient environment 202 via the second opening 114(2) may be enabled. Gas entry 116(1) through the first opening 114(1) may also occur at the first time T1. For example, while the wearable device 102 is secured to the body of the user 106, carbon dioxide from the body of the user 106 may enter the internal volume 110 through the first opening 114(1). In cases where the concentration of gas within the internal volume 110 exceeds that of the ambient environment 202, gas may primarily exit the device housing 108 through the second opening 114(2). In cases where concentrations of gas in the internal volume 110 and ambient environment 202 are generally similar, the gas exchange 118(1) may be small. In some implementations, the valve 120 may be retained in an open state until a rate of change in a quantity or rate of accumulation of carbon dioxide in the internal volume 110, detected using the carbon dioxide sensor 124, is less than a threshold rate of change. In other implementations, as described previously, a purging mechanism may be used to move carbon dioxide from the internal volume 110 toward the ambient environment 202.

At a second time T2, the valve 120 may be moved to the closed position to enable carbon dioxide to accumulate within the internal volume 110. For example, when the valve 120 is closed, gas exchange 118 between the internal volume 110 and the ambient environment 202 may be prevented, such that gas entry 116(2) from the body of the user 106 into the internal volume 110 through the first opening 114(1) causes the amount of accumulated gas 122(1) within the internal volume 110 to increase.

At a third time T3, sensor data 204(1) indicative of the carbon dioxide in the internal volume 110 may be acquired and sent to one or more computing devices 206. In some implementations, after a threshold length of time subsequent to closure of the valve 120 has elapsed, the carbon dioxide sensor 124 may acquire sensor data 204(1) indicative of carbon dioxide in the accumulated gas 122(2). For example, gas entry 116(3) through the first opening 114(1) may continue during the threshold length of time after closure of the valve 120, and the sensor data 204(1) may be indicative of one or more of a quantity of carbon dioxide in the accumulated gas 122(2) or a rate of accumulation of the carbon dioxide. While FIG. 2 depicts the computing device(s) 206 that receive the sensor data 204(1) as devices that are external to the wearable device 102, such as one or more servers, personal computing devices, portable computing devices, and so forth, in other implementations, the wearable device 102 may include one or more processors or other components and may process the sensor data 204(1) to determine a glucose value in addition to or in lieu of use of separate computing devices 206.

The process depicted in FIG. 2 may be repeated multiple times. For example, after determining sensor data 204(1) the valve 120 may be opened to enable gas to exit the device housing 108 through the second opening 114(2), the valve 120 may subsequently be closed to allow gas to accumulate, and additional sensor data 204 may be acquired.

Figure 3:
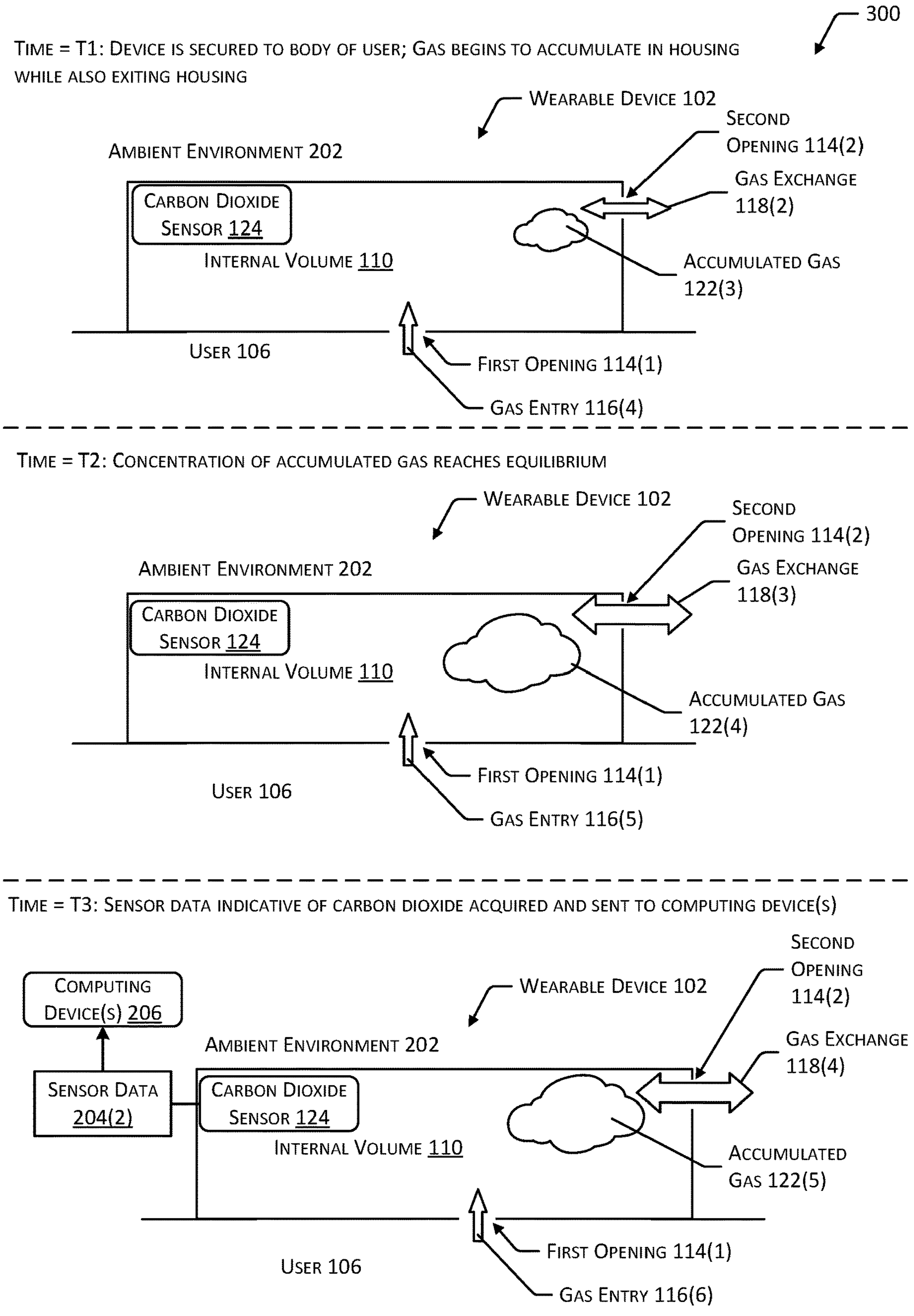
FIG. 3 is a diagram depicting an implementation of a method for determining rates or quantities of transdermal carbon dioxide emitted from the skin of a user that includes determining an equilibrium state for the passage of gas through an opening.

FIG. 3 is a diagram 300 depicting an implementation of a method for determining rates or quantities of transdermal carbon dioxide emitted from the skin of a user 104 that includes determining an equilibrium state for the passage of gas through an opening 114. As described with regard to FIG. 1, in some implementations, the wearable device 102 may include a device housing 108 with a first opening 114(1) positioned adjacent to the body of the user 106 when worn, such that carbon dioxide emitted from the skin of the user 104 may enter the internal volume 110 of the device housing 108 through the first opening 114(1). The device housing 108 may also include a second opening 114(2) that enables the exchange of gas between the internal volume 110 and the ambient environment 202 outside of the device housing 108.

At a first time T1, the wearable device 102 may be secured to the body of a user 106. Gas may then begin to accumulate in the device housing 108 while also exiting the device housing 108 through the second opening 114(2). For example, carbon dioxide emitted from the skin of the user 104 may enter the internal volume 110 through the first opening 114(1). Gas exchange 118(2) between the internal volume 110 and the ambient environment 202 may also occur through the second opening 114(2). During times when the gas entry 116(4) is larger than the amount of gas that exits the internal volume 110 through the second opening 114(2), such as times when metabolism causes carbon dioxide to be emitted from the body of the user 106 into the internal volume 110, accumulated gas 122(3) may begin to fill the internal volume 110. In some implementations, the second opening 114(2) may be sized to restrict the flow of gas from the internal volume 110 to the ambient environment 202 to a known value. In other implementations, the second opening 114(2) may include a membrane or other mechanism that is permeable to carbon dioxide to enable carbon dioxide to exit the internal volume 110 at a known rate. In still other implementations, a carbon dioxide sensor 124 or other gas sensor may be positioned in association with the second opening 114(2) to determine a direction and rate associated with the gas exchange 118(2). For example, a flow meter or flow sensor may be positioned within or in association with the second opening 114(2) to measure passage of gas through the opening 114(2). As described previously with regard to FIG. 2, in some implementations, a pump, fan, piezoelectric device, or other gas-moving mechanism may be used to displace carbon dioxide or other gas from the internal volume 110 toward the ambient environment 202.

At a second time T2, the concentration of accumulated gas 122(4) may reach equilibrium, at which point a rate of change in the amount of carbon dioxide in the internal volume 110, measured using the carbon dioxide sensor 124, is less than a threshold value. For example, when the gas entry 116(5) and the amount of gas that exits the internal volume 110 via gas exchange 118(3) through the second opening 114(2) are similar, the rate of change of the accumulated gas 122(4) may be small.

At a third time T3, sensor data 204(2) indicative of carbon dioxide in the internal volume 110 may be acquired and sent to one or more computing devices 206. As described with regard to FIG. 2, in some implementations, the computing device(s) 206 may include processors, modules, and so forth associated with the wearable device 102 in addition to or in lieu of one or more separate computing devices 206. Sensor data 204 may be acquired using the carbon dioxide sensor 124 at selected time periods, which may be used to determine glucose values for the user 106 associated with different times that may be indicative of glucose metabolism of the user 106 over time. In other implementations, sensor data 204(2) may be acquired in response to determining that the concentration of accumulated gas 122(5) has deviated from the equilibrium state by at least a threshold amount, or a rate of change associated with the accumulated gas 122(5) exceeds a threshold rate of change.

Figure 4:
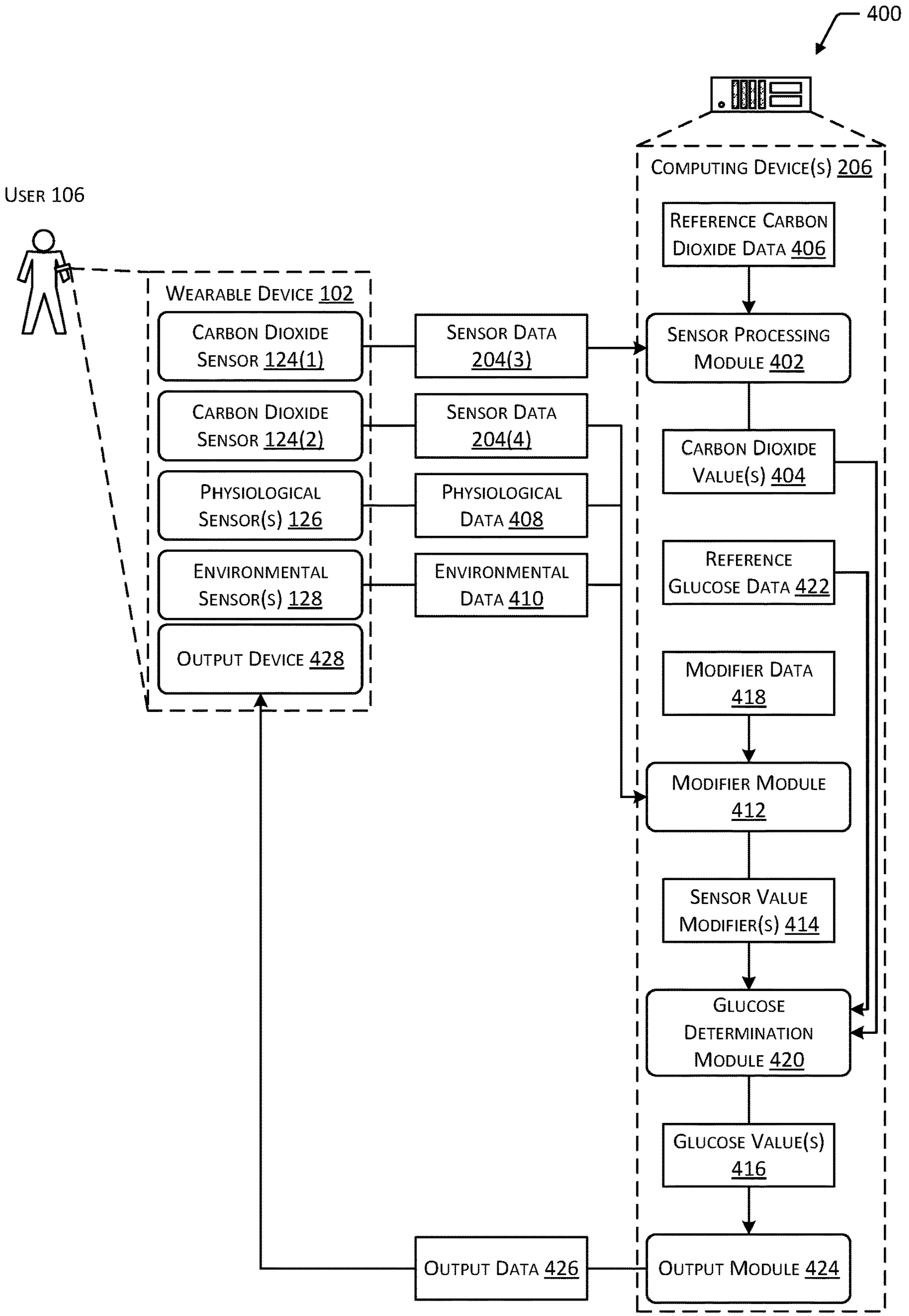
FIG. 4 is a diagram depicting an implementation of a system for determining a value indicative of glucose associated with at least a portion of a body of a user based on carbon dioxide emitted from the skin of the user.

FIG. 4 is a diagram 400 depicting an implementation of a system for determining a value indicative of glucose associated with at least a portion of a body of a user 106 based on carbon dioxide emitted from the skin of the user 104. As described with regard to FIGS. 1-3, a wearable device 102 may include a first carbon dioxide sensor 124(1) that determines sensor data 204(3) indicative of a quantity of carbon dioxide or a rate of accumulation of carbon dioxide within the device housing 108 of the wearable device 102. The sensor data 204(3) may be sent to one or more computing devices 206, which may include a computing device 206 associated with the wearable device 102 or a separate computing device 206. A sensor processing module 402 associated with the computing device(s) 206 may determine one or more carbon dioxide values 404 based on the sensor data 204(3). Carbon dioxide value(s) 404 may include a quantity of carbon dioxide in the internal volume 110 of the wearable device 102, a concentration of the carbon dioxide in the internal volume 110, a rate at which the carbon dioxide accumulates or exits the internal volume 110, and so forth. In some implementations, the sensor processing module 402 may access reference carbon dioxide data 406, which may include relationships between quantities, concentrations, or rates of accumulation of gas in the internal volume 110 and quantities, concentrations, or rates of accumulation of carbon dioxide.

In some implementations, the wearable device 102 may include one or more additional sensors, such as a second carbon dioxide sensor 124(2) for determining sensor data 204(4) indicative of ambient carbon dioxide, one or more physiological sensors 126 for determining physiological data 408 indicative of one or more physiological values associated with the user 106, one or more environmental sensors 128 for determining environmental data 410 indicative of one or more values associated with the ambient environment 202, and so forth. For example, physiological values may include an impedance value indicative of the presence of sweat, a detected quantity of ketone bodies, body temperature, blood oxygenation, and so forth. Environmental values may include ambient temperature, ambient barometric pressure, a detected quantity of ambient carbon dioxide, and so forth. A modifier module 412 associated with the computing device(s) 206 may receive the sensor data 204(4), physiological data 408, environmental data 410, or combinations thereof and determine one or more sensor value modifiers 414 based on this data. For example, a sensor value modifier 414 may be used to modify one or more carbon dioxide values 404 or may be used when determining a glucose value 416 based on the carbon dioxide value(s) 404. In some implementations, the modifier module 412 may access modifier data 418, which may include one or more rules, algorithms, equations, or relationships that associate values represented by the sensor data 204(4), physiological data 408, or environmental data 410 and corresponding sensor value modifiers 414.

A glucose determination module 420 associated with the computing device(s) 206 may determine one or more glucose values 416 based on the carbon dioxide value(s) 404 and the sensor value modifier(s) 414. In some implementations, the glucose determination module 420 may access reference glucose data 422, which may associate carbon dioxide values 404 with corresponding glucose values 416, such as through use of one or more lookup tables. In other implementations, the reference glucose data 422 may indicate one or more rules, algorithms, equations, or relationships that associate carbon dioxide values 404 with glucose values 416. For example, the breakdown of one molecule of glucose typically yields six molecules of carbon dioxide. Based on the carbon dioxide value(s) 404, which may indicate a quantity of accumulated carbon dioxide within the device housing 108 over a selected period of time, or the rate at which the carbon dioxide accumulated, a glucose value 416 indicative of a quantity of metabolized glucose may be determined.

An output module 424 associated with the computing device(s) 206 may generate output data 426 based on the glucose value(s) 416. The output data 426 may include the glucose value(s) 416 themselves, one or more instructions based on the glucose value(s) 416, an indication of a change in glucose value(s) 416 over time, and so forth. The output data 426 may be provided to one or more output devices 428 associated with the wearable device 102 for output. For example, an output device 428 may include one or more displays or speakers. In other implementations, the output data 426 may include one or more other metabolic values, such as a total metabolic value that may reflect metabolism of glucose as well as other substances that are able to be metabolized.

Figure 5:
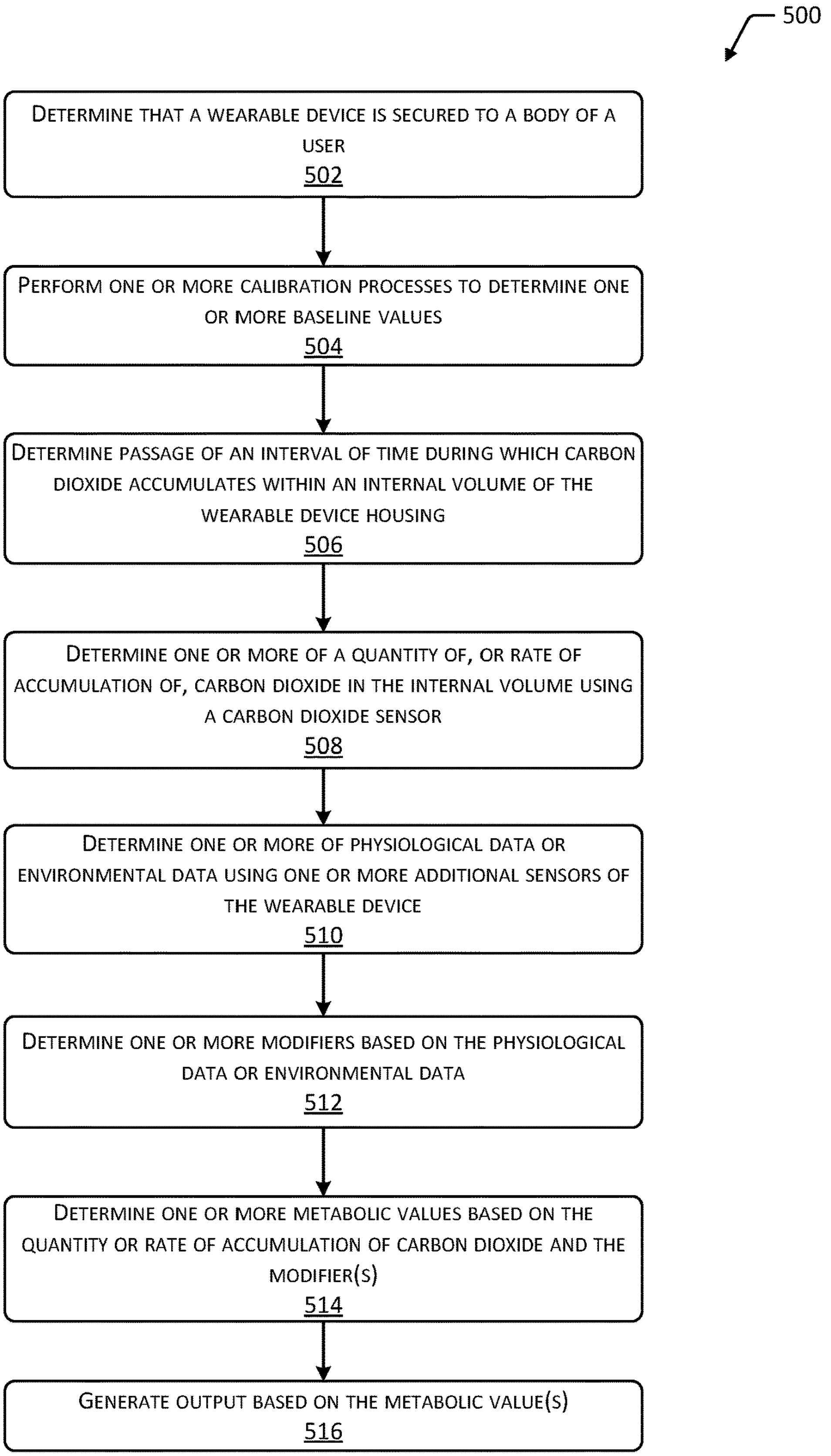
FIG. 5 is a flow diagram depicting an implementation of a method for determining glucose values or other metabolic values based on rates or quantities of transdermal carbon dioxide emitted from the skin of a user.

FIG. 5 is a flow diagram 500 depicting an implementation of a method for determining glucose values 416 or other metabolic values based on rates or quantities of transdermal carbon dioxide emitted from the skin of a user 104. At 502, a determination may be made that a wearable device 102 is secured to the body of a user 106. For example, a wearable device 102 may include one or more contact sensors that detect contact or near-contact with the skin of a user 104. Continuing the example, one or more capacitive or pressure sensors may detect placement of the wearable device 102 against or proximate to the body of the user 106. As another example, a wearable device 102 may include one or more sensors that detect closure of a fastener. In other implementations, detection of physiological values or at least a threshold quantity of carbon dioxide by one or more sensors of the wearable device 102 may be used to infer that the wearable device 102 has been secured to the body of a user 106.

At 504, one or more calibration processes may be performed to determine one or more baseline values. For example, relationships between signal values determined using a carbon dioxide sensor 124 and physiological characteristics of the user 106, such as body temperature, may be determined over time, and a set of user-specific coefficients, rules, algorithms, and so forth that may be used to determine and compensate for the effect of physiological values on data determined using the carbon dioxide sensor 124. In one implementation, a calibration process may include application of pressure to the skin of the user 104 using a portion of the wearable device 102, such as an inflatable or movable band or cuff. Pressure applied to the body of the user 106 at the location of the wearable device 102 may affect emission of carbon dioxide, and values associated with carbon dioxide before, during, or after application of pressure may be used to calibrate subsequent measurements associated with carbon dioxide for the user 106. In some implementations, one or more other physiological values under application of pressure, such as a blood pressure value, may be determined, and a relationship between blood pressure and carbon dioxide may be used to calibrate the sensors of the wearable device 102.

At 506, passage of an interval of time may be determined during which carbon dioxide accumulates within an internal volume 110 of the device housing 108 of the wearable device 102. In some implementations, the internal volume 110 may be at least partially emptied of carbon dioxide by opening a valve 120, then the valve 120 may be closed to enable accumulation of carbon dioxide within the internal volume 110. In other implementations, the device housing 108 may lack one or more valves 120, and carbon dioxide may accumulate within the internal volume 110 until an equilibrium state with the ambient environment 202 is reached and a rate of change in the quantity of accumulated gas 122 in the internal volume 110 is less than a threshold value. In still other implementations, determination of a deviation from an equilibrium state between the internal volume 110 and the ambient environment 202 by at least a threshold amount, or a rate of change greater than a threshold rate of change, may be determined.

At 508, one or more of a quantity of, or rate of accumulation of, carbon dioxide in the internal volume 110 may be determined using a carbon dioxide sensor 124. For example, sensor data 204 from one or more carbon dioxide sensors 124 may be used to determine carbon dioxide values 404 indicative of quantities or rates associated with carbon dioxide in the device housing 108. In some implementations, multiple carbon dioxide values 404 may be determined sequentially to improve accuracy and reduce the effect of noise. In other implementations, multiple carbon dioxide sensors 124 may be secured to different portions of the body of the user 106, and multiple carbon dioxide values 404 may be determined to improve accuracy and reduce the effect of variation in tissue within the body on the resulting glucose value(s) 416.

At 510, one or more of physiological data 408 or environmental data 410 may be determined using one or more additional sensors of the wearable device 102. For example, additional sensors may include carbon dioxide sensors 124 for determining ambient carbon dioxide, temperature sensors for determining body temperature or ambient temperature, blood oxygen sensors, heart rate sensors, respiratory rate sensors, PPGs, accelerometers, moisture sensors, location sensors, and so forth.

At 512, one or more modifiers may be determined based on the physiological data 408 or environmental data 410. As described with regard to FIG. 4, physiological data 408, environmental data 410, or combinations thereof may be used to determine one or more sensor value modifiers 414. Sensor value modifiers 414 may be used to modify one or more carbon dioxide values 404 or may be used when determining a glucose value 416 based on the carbon dioxide value(s) 404. Modifier data 418 may indicate one or more rules, algorithms, equations, or relationships that associate physiological or environmental values with corresponding sensor value modifiers 414.

At 514, one more metabolic values may be determined based on the quantity or rate of accumulation of carbon dioxide and the determined modifiers. As described with regard to FIG. 4, based on one or more carbon dioxide values 404, and in some implementations one or more sensor value modifiers 414, a glucose value 416 may be determined, such as through use of reference glucose data 422 that associates carbon dioxide values 404 with glucose values 416. In some implementations, reference glucose data 422 may include one or more rules, algorithms, equations, or relationships that associate carbon dioxide values 404 with glucose values 416. In other implementations, metabolism of other substances, such as fat or protein, may be determined. For example, one or more physiological sensors 126 may include a ketone sensor, which may determine a quantity or rate of accumulation associated with ketones. This value may be used to determine a quantity or rate associated with metabolism of fat. In some implementations, a value indicative of metabolism of multiple substances may be determined based on a carbon dioxide value 404, and data from a ketone sensor may be used to determine a modifier, which in combination with the value indicative of metabolism may be used to determine a glucose value 416 indicative of metabolism of glucose. For example, the nutritional state of a user, the size of adipose cells of the user, and so forth may affect both basal glucose metabolism and insulin-influenced glucose metabolism. In some implementations, a determined metabolic value may be indicative of the diet or nutritional state of the user, the amount or size of adipose cells, and so forth.

At 516, output may be generated based on the metabolic value(s). The output may include audio output, visual output, or combinations thereof. The output may include the metabolic value(s) or other information determined based on the value(s) such as rate of change or differences between multiple values, an instruction based on one or more metabolic values, and so forth.

Figure 6:
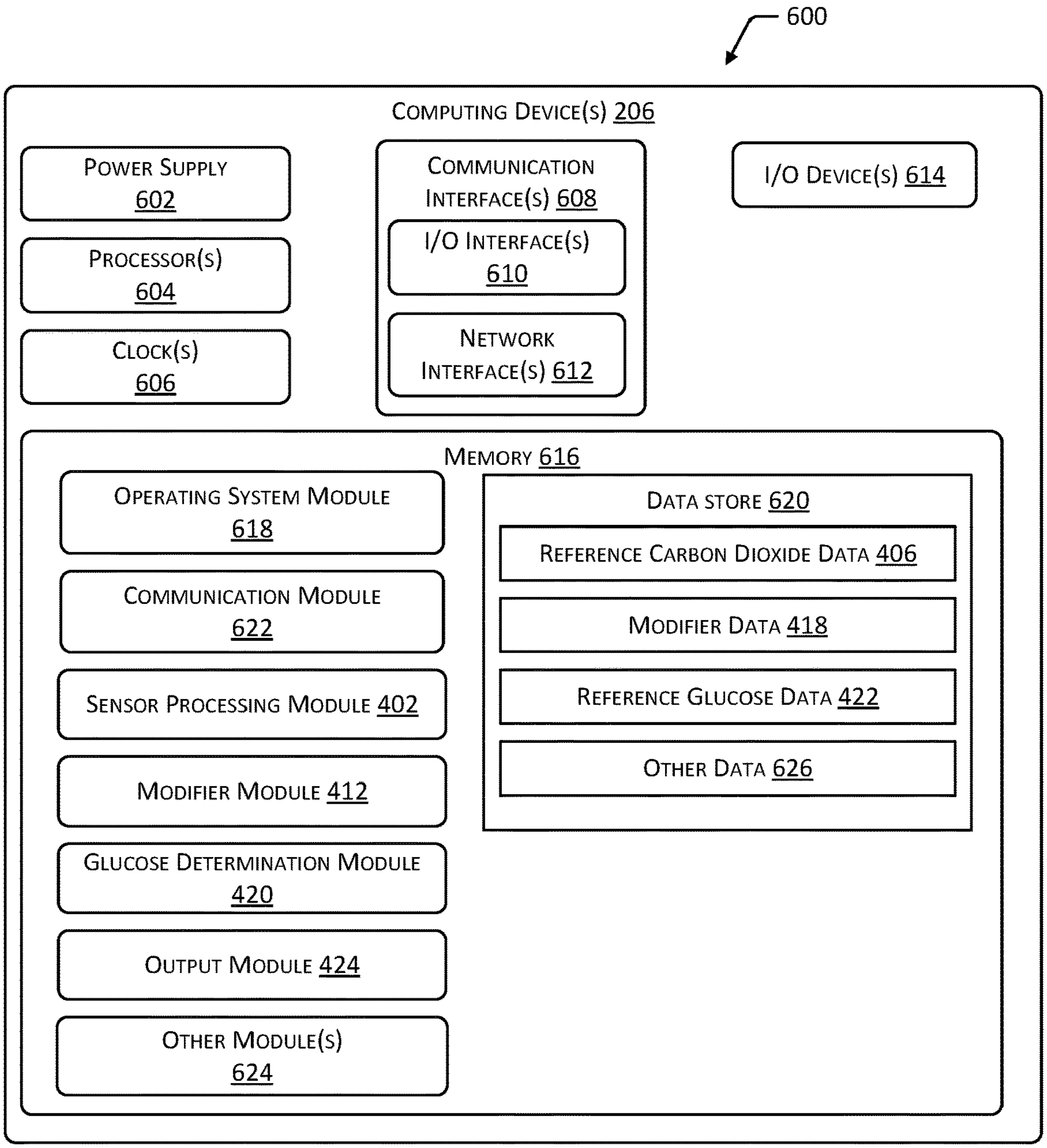
FIG. 6 is a block diagram depicting an implementation of a computing device within the present disclosure.

FIG. 6 is a block diagram depicting 600 an implementation of a computing device 206 within the present disclosure. In some implementations, the computing device 206 may include one or more servers or other types of computing devices 206 used to process data from wearable devices 102 and determining data based on the data. In other implementations, the computing devices 206 may include wearable devices 102 and use of a separate server or other type of computing device 206 may be omitted. In other cases, combinations of servers and wearable devices 102 may be used to perform the functions described herein. Therefore, while FIG. 6 depicts a single block diagram 600 of a computing device 206, any number and any type of computing devices 206 may be used to perform the functions described herein.

One or more power supplies 602 may be configured to provide electrical power suitable for operating the components of the computing device 206. In some implementations, the power supply 602 may include a rechargeable battery, fuel cell, photovoltaic cell, power conditioning circuitry, and so forth.

The computing device 206 may include one or more hardware processor(s) 604 (processors) configured to execute one or more stored instructions. The processor(s) 604 may include one or more cores. One or more clock(s) 606 may provide information indicative of date, time, ticks, and so forth. For example, the processor(s) 604 may use data from the clock 606 to generate a timestamp, trigger a preprogrammed action, and so forth. Continuing the example, based on data from a clock 606, passage of a determined interval of time for accumulation of carbon dioxide within a wearable device 102, or establishment of equilibrium between an internal volume 110 and the ambient environment 202, may be determined.

The computing device 206 may include one or more communication interfaces 608, such as input/output (I/O) interfaces 610, network interfaces 612, and so forth. The communication interfaces 608 may enable the computing device 206, or components of the computing device 206, to communicate with other computing devices 206 or components of the other computing devices 206. The I/O interfaces 610 may include interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 610 may couple to one or more I/O devices 614. The I/O devices 614 may include any manner of input devices or output devices associated with the computing device 206. For example, I/O devices 614 may include touch sensors, displays, touch sensors integrated with displays (e.g., touchscreen displays), keyboards, mouse devices, microphones, image sensors, cameras, scanners, speakers or other types of audio output devices, haptic devices, printers, and so forth. I/O devices 614 may also include sensors that may be integrated within, or in wired or wireless communication with, one or more computing devices 206. Example sensors may include one or more of a carbon dioxide sensor 124, physiological sensor 126, or environmental sensor 128.

The network interfaces 612 may be configured to provide communications between the computing device 206 and other devices, such as the I/O devices 614, routers, access points, and so forth. The network interfaces 612 may include devices configured to couple to one or more networks including local area networks (LANs), wireless LANs (WLANs), wide area networks (WANs), wireless WANs, and so forth. For example, the network interfaces 612 may include devices compatible with Ethernet, Wi-Fi, Bluetooth, ZigBee, Z-Wave, 5G, LTE, and so forth.

The computing device 206 may include one or more buses or other internal communications hardware or software that allows for the transfer of data between the various modules and components of the computing device 206.

As shown in FIG. 6, the computing device 206 may include one or more memories 616. The memory 616 may include one or more computer-readable storage media (CRSM). The CRSM may be any one or more of an electronic storage medium, a magnetic storage medium, an optical storage medium, a quantum storage medium, a mechanical computer storage medium, and so forth. The memory 616 may provide storage of computer-readable instructions, data structures, program modules, and other data for the operation of the computing device 206. A few example modules are shown stored in the memory 616, although the same functionality may alternatively be implemented in hardware, firmware, or as a system on a chip (SoC).

The memory 616 may include one or more operating system (OS) modules 618. The OS module 618 may be configured to manage hardware resource devices such as the I/O interfaces 610, the network interfaces 612, the I/O devices 614, and to provide various services to applications or modules executing on the processors 604. The OS module 618 may implement a variant of the FreeBSD operating system as promulgated by the FreeBSD Project; UNIX or a UNIX-like operating system; a variation of the Linux operating system as promulgated by Linus Torvalds; the Windows operating system from Microsoft Corporation of Redmond, Washington, USA; or other operating systems.

One or more data stores 620 and one or more of the following modules may also be associated with the memory 616. The modules may be executed as foreground applications, background tasks, daemons, and so forth. The data store(s) 620 may use a flat file, database, linked list, tree, executable code, script, or other data structure to store information. In some implementations, the data store(s) 620 or a portion of the data store(s) 622 may be distributed across one or more other devices including other computing devices 602, network attached storage devices, and so forth.

A communication module 622 may be configured to establish communications with one or more other computing devices 206. Communications may be authenticated, encrypted, and so forth.

The memory 616 may also store the sensor processing module 402. The sensor processing module 402 may determine one or more carbon dioxide values 404 based on the sensor data 204 from a carbon dioxide sensor 124. Carbon dioxide value(s) 404 may include a quantity of carbon dioxide in the internal volume 110 of the device housing 108 of the wearable device 102, a concentration of the carbon dioxide in the internal volume 110, a rate at which the carbon dioxide accumulates or exits the internal volume 110, and so forth. In some implementations, the sensor processing module 402 may access reference carbon dioxide data 406, which may include relationships between quantities, concentrations, or rates of accumulation of gas in the internal volume 110 and quantities, concentrations or rates of accumulation of carbon dioxide.

The memory 616 may additionally store the modifier module 412. The modifier module 412 may determine one or more sensor value modifiers 414 based on data from carbon dioxide sensors 124, physiological sensors 126, environmental sensors 128, and so forth. A sensor value modifier 414 may be used to modify one or more carbon dioxide values 404 or may be used when determining a glucose value 416 based on the carbon dioxide value(s) 404. In some implementations, the modifier module 412 may access modifier data 418, which may include one or more rules, algorithms, equations, or relationships that associate values represented by sensor data 204, physiological data 408, or environmental data 410 and corresponding sensor value modifiers 414.

The memory 616 may store the glucose determination module 420. The glucose determination module 420 may determine one or more glucose values 416 based on carbon dioxide value(s) 404, and in some implementations based on one or more sensor value modifier(s) 414. In some implementations, the glucose determination module 420 may access reference glucose data 422, which may associate carbon dioxide values 404 with corresponding glucose values 416, such as through use of one or more lookup tables. In other implementations, the reference glucose data 422 may indicate one or more rules, algorithms, equations, or relationships that associate carbon dioxide values 404 with glucose values 416.

The memory 618 may also store the output module 424. The output module 424 may generate output data 426 based on one or more glucose values 416. The output data 426 may include the glucose value(s) 416, one or more instructions based on the glucose value(s) 416, an indication of a change in glucose value(s) 416 over time, or other values determined based on one or more glucose values 416.

Other modules 624 may also be present in the memory 616. For example, other modules 624 may include permission or authorization modules to enable users 106 to access and modify data associated with the computing device 206. Other modules 624 may include permission modules to enable a user 106 to opt in or otherwise provide authorization for data associated with a sensors and other components of wearable devices 102 to be acquired, sent to other computing devices 206, and so forth. Other modules 624 may also include encryption modules to encrypt and decrypt communications between computing devices 206, authentication modules to authenticate communications sent or received by computing devices 206, user interface modules to generate interfaces for receiving input from users 106 and presenting output, and so forth. Other modules 624 may include modules for performing calibration processes and determining baseline values and other calibration values, weights, modifiers, coefficients, and so forth based on historical data associated with a user 106 or with a wearable device 102.

Other data 626 within the data store(s) 620 may include configurations, settings, preferences, and default values associated with computing devices 206. Other data 626 may also include encryption keys and schema, access credentials, and so forth. Other data 626 may include user data indicative of characteristics of a user 106 such as an age, height, weight, or other physiological or demographic information input by a user 106. Other data 626 may include historical data indicative of previous physiological values, environmental values, carbon dioxide values 404, and glucose values 416, which may be used as calibration data or baseline values for determining subsequent values.

The processes discussed in this disclosure may be implemented in hardware, software, or a combination thereof. In the context of software, the described operations represent computer-executable instructions stored on one or more computer-readable storage media that, when executed by one or more hardware processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described in this disclosure. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as exemplary forms of implementing the claims.

What is claimed is:

1. A system comprising:
- a wearable device comprising:
  - a housing having:
    - an internal volume;
    - a first side;
    - a second side;
    - a first opening in the first side, wherein the first opening faces a body of a user when the wearable device is worn and enables passage of carbon dioxide from the body of the user into the internal volume; and
    - a second opening in the second side, wherein the second opening enables passage of carbon dioxide from the internal volume to an ambient environment external to the housing;
  - a first carbon dioxide sensor within the housing, wherein the first carbon dioxide sensor determines first sensor data indicative of a first quantity of carbon dioxide within the internal volume; and
  - a valve in the second opening; and
- one or more memories storing computer-executable instructions; and
- one or more hardware processors to execute the computer-executable instructions to:
  - at a first time, open the valve to enable carbon dioxide within the internal volume to pass through the second opening;
  - at a second time after the first time, close the valve to prevent passage of carbon dioxide through the second opening;
  - at a third time after the second time, determine that a threshold length of time associated with accumulation of carbon dioxide in the internal volume has elapsed;
  - determine the first quantity of carbon dioxide based on the first sensor data in response to the elapsing of the threshold length of time, wherein the first quantity of carbon dioxide is indicative of carbon dioxide emitted from skin of the user through the first opening in the housing;
  - determine a metabolized glucose value based on the first quantity of carbon dioxide and lookup data, wherein the lookup data associates the first quantity of carbon dioxide with the metabolized glucose value; and
  - generate output based on the metabolized glucose value.

2. The system of claim 1, further comprising:
- a second carbon dioxide sensor, wherein the second carbon dioxide sensor determines second sensor data indicative of a second quantity of carbon dioxide external to the housing, and wherein the metabolized glucose value is further determined based on a difference between the first quantity of carbon dioxide and the second quantity of carbon dioxide.

3. The system of claim 1, further comprising:
- one or more second sensors that determine second sensor data indicative of one or more of: a physiological value associated with the user, or an environmental value associated with an ambient environment external to the wearable device.

4. The system of claim 1, further comprising:
- one or more gas-moving devices that move carbon dioxide from the internal volume of the housing towards the second opening.

5. The system of claim 1, further comprising:
- one or more second sensors, wherein the one or more second sensors include one or more of a temperature sensor, a blood oxygen sensor, a heart rate sensor, a respiratory rate sensor, a photoplethysmograph (PPG), an accelerometer, a moisture sensor, a sweat sensor, a ketone sensor, or a pressure sensor that determines a pressure applied by the wearable device to the user.

6. The system of claim 1, the one or more hardware processors to further execute the computer-executable instructions to:

determine that a rate of change in the first quantity of carbon dioxide is less than a threshold rate of change, wherein the metabolized glucose value is determined in response to the rate of change being less than the threshold rate of change.

7. A system comprising:

a wearable device comprising:

a housing having an internal volume and a first opening that enables passage of carbon dioxide from skin of a user into the internal volume;

a second opening in the housing, wherein carbon dioxide passes between the internal volume of the housing and an exterior of the housing through the second opening;

a valve in the second opening, wherein the valve is moveable between an open position in which gas passes between the internal volume of the housing and the exterior of the housing and a closed position that prevents passage of gas between the internal volume of the housing and the exterior of the housing;

a first carbon dioxide sensor that determines first sensor data indicative of carbon dioxide emitted from the skin of the user; and a second carbon dioxide sensor that determines second sensor data indicative of carbon dioxide external to the housing;

one or more memories storing computer-executable instructions; and one or more hardware processors to execute the computer-executable instructions to:

at a first time, cause the valve to open to enable carbon dioxide within the housing to pass through the second opening;

at a second time after the first time, cause the valve to close to prevent passage of carbon dioxide through the second opening;

at a third time that is a threshold interval after the second time, determine, based on the first sensor data, one or more of a first quantity of carbon dioxide or a first rate of emission of carbon dioxide, wherein the one or more of the first quantity of carbon dioxide or the first rate of emission of carbon dioxide includes one or more of a quantity of carbon dioxide within the internal volume of the housing or a rate of accumulation of carbon dioxide within the internal volume of the housing;

determine a metabolic value based on:

the one or more of the first quantity of carbon dioxide or the first rate of emission of carbon dioxide, data indicative of one or more relationships between emission of carbon dioxide from skin and metabolism of one or more substances, and the second sensor data; and generate output based on the metabolic value.

8. The system of claim 7, wherein:

passage of carbon dioxide through the second opening affects the one or more of the first quantity of carbon dioxide or the first rate of emission of carbon dioxide determined based on the first sensor data; and the one or more hardware processors to further execute the computer-executable instructions to:

determine that a rate of change in the one or more of the first quantity of carbon dioxide or the first rate of emission of carbon dioxide is less than a threshold rate of change, wherein the metabolic value is determined in response to the rate of change being less than the threshold rate of change.

9. The system of claim 7, further comprising computer-executable instructions to:

at a fourth time after the third time, cause the valve to open;

at a fifth time after the fourth time, cause the valve to close; and at a sixth time that is a threshold interval after the fifth time, determine, based on data from the first carbon dioxide sensor, one or more of a second quantity of carbon dioxide or a second rate of emission of carbon dioxide, wherein the metabolic value is further determined based on the one or more of the second quantity of carbon dioxide or the second rate of emission of carbon dioxide.

10. The system of claim 7, further comprising:

one or more physiological sensors that determine third sensor data indicative of one or more physiological values of the user associated with respiration; and the one or more hardware processors to further execute the computer-executable instructions to:

determine a modifier associated with the one or more of the first quantity of carbon dioxide or the first rate of emission of carbon dioxide based on the third sensor data;

wherein the metabolic value is further determined based on the modifier.

11. The system of claim 10, wherein the one or more physiological sensors include one or more of a temperature sensor, a blood oxygen sensor, a heart rate sensor, a respiratory rate sensor, a photoplethysmograph (PPG), an accelerometer, a moisture sensor, a sweat sensor, a ketone sensor, or a pressure sensor that determines a pressure applied by the wearable device to the user.

12. The system of claim 4, further comprising:

one or more environmental sensors that determine third sensor data indicative of one or more of: an ambient temperature external to the wearable device, or an ambient pressure external to the wearable device; and determine a modifier associated with the one or more of the first quantity of carbon dioxide or the first rate of emission of carbon dioxide based on the third sensor data;

wherein the metabolic value is further determined based on the modifier.

13. The system of claim 7, further comprising:

one or more motion sensors that determine third sensor data indicative of movement of the wearable device; and the one or more hardware processors to further execute the computer-executable instructions to:

determine, based on the third sensor data, that the movement is greater than a threshold value; and in response to the movement being greater than the threshold value, determine, based on the third sensor data, a modifier associated with the one or more of the first quantity of carbon dioxide or the first rate of emission of carbon dioxide based on the second sensor data;

wherein the metabolic value is further determined based on the modifier.

14. The system of claim 7, wherein:

the first carbon dioxide sensor is positioned at a first location on the skin of the user, the second carbon dioxide sensor is positioned at a second location on the skin of the user; and the one or more hardware processors to further execute the computer-executable instructions to:

determine one or more of a second quantity of carbon dioxide or a second rate of emission of carbon dioxide based on the second sensor data determined using the second carbon dioxide sensor, wherein the metabolic value is further determined based on the one or more of the second quantity of carbon dioxide or the second rate of emission of carbon dioxide.

15. A system comprising:

a wearable device comprising:

a first sensor that determines first sensor data indicative of carbon dioxide emitted from skin of a user;

a housing that encloses the first sensor, wherein the housing has an internal volume, a first opening, and a second opening, and the carbon dioxide emitted from the skin of the user passes through the first opening into the internal volume;

a valve in the second opening wherein the valve is movable between an open position in which gas passes between the internal volume and an ambient environment and a closed position that prevents passage of gas between the internal volume and the ambient environment; and one or more second sensors that determine second sensor data indicative of one or more of: a physiological value associated with the user, or an environmental value associated with an ambient environment external to the wearable device;

one or more memories storing computer-executable instructions; and one or more hardware processors to execute the computer-executable instructions to:

at a first time, cause the valve to open to enable carbon dioxide within the housing to pass through the second opening;

at a second time after the first time, cause the valve to close to prevent passage of carbon dioxide through the second opening;

at a third time after the second time, determine that a threshold length of time associated with accumulation of carbon dioxide in the housing has elapsed;

determine one or more of a first quantity of carbon dioxide or a first rate of emission of carbon dioxide based on the first sensor data, wherein the one or more of the first quantity of carbon dioxide or the first rate of emission of carbon dioxide is determined based on the first sensor data in response to the elapsing of the threshold length of time;

determine a modifier to the one or more of the first quantity of carbon dioxide or the first rate of emission of carbon dioxide based on the second sensor data;

determine a metabolic value based on the modifier, the one or more of the first quantity of carbon dioxide or the first rate of emission of carbon dioxide, and data indicative of one or more relationships between emission of carbon dioxide from skin and metabolism of one or more substances; and generate output based on the metabolic value.

16. The system of claim 15, the one or more hardware processors to further execute the computer-executable instructions to:

determine that a rate of change in the one or more of the first quantity of carbon dioxide or the first rate of emission of carbon dioxide is less than a threshold rate of change, wherein the metabolic value is determined in response to the rate of change being less than the threshold rate of change.

17. The system of claim 16, wherein at least one sensor of the one or more second sensors determines second sensor data indicative of carbon dioxide external to the housing.

18. The system of claim 16, further comprising:

one or more gas-moving devices that move carbon dioxide from the internal volume of the housing toward the second opening.

19. The system of claim 15, wherein the one or more second sensors include one or more of a temperature sensor, a blood oxygen sensor, a heart rate sensor, a respiratory rate sensor, a photoplethysmograph (PPG), an accelerometer, a moisture sensor, a sweat sensor, a ketone sensor, or a pressure sensor that determines a pressure applied by the wearable device to the user.

* * * * *